US011020345B2

(12) United States Patent
Fox et al.

(10) Patent No.: US 11,020,345 B2
(45) Date of Patent: Jun. 1, 2021

(54) NANOSTRAW DEVICES AND METHODS OF FABRICATING AND USING THE SAME

(71) Applicants: The Regents of the University of California, Oakland, CA (US); The Board of Trustees of the Leland Stanford Junior University, Stanford, CA (US)

(72) Inventors: Cade B. Fox, San Francisco, CA (US); Hariharasudhan Chirra Dinakar, San Francisco, CA (US); Nicholas A. Melosh, Stanford, CA (US); Tejal A. Desai, San Francisco, CA (US)

(73) Assignee: The Regents of the University of California The Board of Trustees of the Leland Stanford Junior University Stanford, Stanford, CA (US)

( * ) Notice: Subject to any disclaimer, the term of this patent is extended or adjusted under 35 U.S.C. 154(b) by 177 days.

(21) Appl. No.: 16/083,758

(22) PCT Filed: Mar. 14, 2017

(86) PCT No.: PCT/US2017/022318
§ 371 (c)(1),
(2) Date: Sep. 10, 2018

(87) PCT Pub. No.: WO2017/160850
PCT Pub. Date: Sep. 21, 2017

(65) Prior Publication Data
US 2019/0125668 A1 May 2, 2019

Related U.S. Application Data

(60) Provisional application No. 62/308,035, filed on Mar. 14, 2016.

(51) Int. Cl.
*A61K 9/00* (2006.01)
*B31D 3/00* (2017.01)
(Continued)

(52) U.S. Cl.
CPC .......... *A61K 9/0097* (2013.01); *A61K 9/0053* (2013.01); *A61K 38/28* (2013.01);
(Continued)

(58) Field of Classification Search
CPC .... A61K 9/0097; A61K 38/28; A61K 9/0053; B81C 1/00047; B81C 1/00111;
(Continued)

(56) References Cited

U.S. PATENT DOCUMENTS

| 2004/0094503 A1* | 5/2004 | Ozeryansky | C23F 1/04 216/2 |
| 2006/0280645 A1* | 12/2006 | Sellers | A61L 2/087 422/22 |

(Continued)

OTHER PUBLICATIONS

Fischer et al. (2009) "Biomimetic Nanowire Coatings for Next Generation Adhesive Drug Delivery Systems" Nano Letters 9(2): 716-720.
(Continued)

*Primary Examiner* — Amber R Stiles
(74) *Attorney, Agent, or Firm* — Edward J. Baba; Shweta Chandra; Bozicevic, Field & Francis LLP

(57) ABSTRACT

Microdevices containing a chamber bound on one side by a nanoporous membrane are provided. The nanoporous membrane may contain hollow nanotubes that extend through the nanoporous membrane, from one surface to the other, and extend beyond the surface of the nanoporous membrane opposite the surface interfacing with the chamber. The nanotubes may provide a fluidic conduit between an environment external to the microdevice and the chamber, which (Continued)

is otherwise substantially fluid-tight. Also provided are methods of making a microdevice and methods of using the microdevices.

16 Claims, 8 Drawing Sheets

(51) Int. Cl.
    *B81C 1/00*     (2006.01)
    *A61K 38/28*     (2006.01)
    *B81B 1/00*     (2006.01)

(52) U.S. Cl.
    CPC ............... *B31D 3/00* (2013.01); *B81B 1/008* (2013.01); *B81C 1/00047* (2013.01); *B81C 1/00111* (2013.01); *B81B 2203/0315* (2013.01); *B81B 2203/0361* (2013.01)

(58) Field of Classification Search
    CPC ............ B81B 1/008; B81B 2203/0361; B81B 2203/0315; B31D 3/00; A61M 37/0015; A61M 2037/0023; A61M 2037/003; A61M 2037/0053; A61M 2037/0061
    See application file for complete search history.

(56) References Cited

U.S. PATENT DOCUMENTS

| | | |
|---|---|---|
| 2009/0157166 A1 | 6/2009 | Singhal et al. |
| 2012/0276573 A1* | 11/2012 | VanDersarl .......... C12N 5/0075 435/29 |
| 2015/0258018 A1 | 9/2015 | Martin et al. |
| 2016/0201030 A1 | 7/2016 | Vandersarl et al. |

OTHER PUBLICATIONS

Vandersarl et al, (2012) "Nanostraws for Direct Fluidic Intracellular Access" Nano Letters 12(8): 3881-3886.

* cited by examiner

NANOSTRAW DEVICES AND METHODS OF FABRICATING AND USING THE SAME

CROSS-REFERENCE TO RELATED APPLICATIONS

This application claims the benefit of U.S. Provisional Patent Application No. 62/308,035 filed Mar. 14, 2016, which application is incorporated herein by reference in its entirety.

INTRODUCTION

While the oral route of drug administration provides ease of use and is low cost, the physiological barriers of the gastrointestinal (GI) tract prevent the uptake of intact biological therapeutics and many small molecule drugs. Specifically, metabolic enzymes present throughout the GI tract and the low pH of the stomach degrade drugs, and the intestinal epithelium and its adherent mucus layer prevent permeation of drugs with high molecular weight and/or high polarity. Additionally, many drugs suffer from low solubility, preventing adequate dissolution within the small intestine, the primary site of systemic drug uptake.

Microfabrication techniques of the semiconductor industry can be used to manufacture en masse, reproducible, monodispersed, microdevice platforms for delivery, e.g., oral delivery, of pharmaceuticals.

SUMMARY

Microdevices containing a chamber bound on one side by a nanoporous membrane are provided. The nanoporous membrane may contain hollow nanotubes that extend through the nanoporous membrane, from one surface of the nanoporous membrane to the other, and extend beyond the surface of the nanoporous membrane opposite the surface interfacing with the chamber. The nanotubes may provide a fluidic conduit between an environment external to the microdevice and the chamber, which is otherwise substantially fluid-tight.

A microdevice of the present disclosure may include: a first surface comprising a first region interfacing with the chamber; a second surface opposite the first surface; and a plurality of hollow nanotubes that extend through the nanoporous membrane from the first surface to a distance above the second surface, wherein at least some of the nanotubes extend from within the first region and provide a fluidic conduit between an environment external to the microdevice and the chamber, which is otherwise substantially fluid-tight.

In any embodiment, the microdevice may be a planar device defining a plane, wherein the nanoporous membrane is substantially parallel to the plane. In some embodiments, the microdevice has a ratio between an average lateral dimension and a thickness of 2:1 or greater. In some embodiments, the microdevice has a thickness of 1,000 µm or less. In some embodiments, the microdevice is a substantially circular disc.

In any embodiment, the chamber may have a volume in the range of $10^2$ to $10^6$ µm$^3$.

In any embodiment, the nanotubes may have an inner diameter in the range of 5 to 1,000 nm.

In any embodiment, the distance above the second surface may be in the range of 10 nm to 100 µm.

In any embodiment, the nanoporous membrane may contain the plurality of nanotubes at a density in the range of $10^6$ to $10^9$ cm$^{-2}$.

In any embodiment, the microdevice may include a layer of a first polymeric material, wherein the layer forms one or more second sides bounding the chamber. In some embodiments, the first polymeric material is selected from poly (methyl methacrylate) (PMMA), polydimethylsiloxane (PDMS), polycarbonate (PC), polyethylene terephthalate (PET), chitosan, poly(lactic-co-glycolic acid) (PLGA), poly-2-hydroxyethyl methacrylate (polyHEMA), polystyrene (PS), polyethylene glycol diacrylate-based hydrogels (PEGDA), co-polymers, mixtures, adducts, or combinations thereof. In some embodiments, the nanoporous membrane is bonded to the first polymeric material of the one or more second sides via a heat-activated, pressure-sensitive adhesive. In some embodiments, the heat-activated, pressure-sensitive adhesive is selected from polycaprolactone (PCL), poly-L-lactide (PLLA), poly-DL-lactic acid (DL-PLA), polyglycolic acid (PGA), gelatin, agarose, poly(anhydrides), or co-polymers, mixtures, adducts, or combinations thereof.

In any embodiment, the nanoporous membrane may include a second polymeric material. In some embodiments, the second polymeric material is selected from polycarbonate (PC), polyethylene terephthalate (PET), polylactic acid (PLA), polyglycolic acid (PGA), PLGA, layer-by-layer polyethylene imine/polyacrylic acid, N-isopropylacrylamide (NiPAAM), poly(methyl methacrylate) (PMMA), chitosan, protein hydrogels, or a combination thereof.

In any embodiment, the nanoporous membrane may be bonded to components of the microdevice via one or more second regions of only the first surface.

Also provided herein is a method of preparing a microdevice, the method including: i) fabricating on a substrate a first layer containing an open chamber having a bottom surface and one or more lateral partitions that extend away from the substrate, wherein one or more exposed ends of the one or more lateral partitions distal to the bottom surface define a top surface of the first layer and circumscribe an opening at the top of the chamber; ii) bonding a nanoporous membrane to the top surface, thereby forming a fluid-tight seal between the top surface and the nanoporous membrane, wherein the nanoporous membrane includes: a first surface containing a first region interfacing with the chamber; and a second surface opposite the first surface; and a plurality of hollow nanotubes that extend through the nanoporous membrane from the first surface to the second surface; iii) patterning the first layer and the nanoporous membrane bonded to the top surface; and iv) removing a sublayer of the patterned nanoporous membrane, thereby forming a third surface of the nanoporous membrane opposite the first surface, wherein the nanotubes extend through the nanoporous membrane from the first surface to a distance above the third surface, wherein at least some of the nanotubes extend from within the first region and provide a fluidic conduit between an environment external to the microdevice and the chamber, which is otherwise substantially fluid-tight. In some embodiments, the bonding includes: depositing a second layer of a heat-activated, pressure-sensitive adhesive on the top surface; and heat bonding the nanoporous membrane to the top surface. In some embodiments, the heat-activated, pressure-sensitive adhesive is polycaprolactone (PCL), poly-L-lactide (PLLA), poly-DL-lactic acid (DL-PLA), polyglycolic acid (PGA), gelatin, agarose, poly (anhydrides), or co-polymers, mixtures, adducts, or combinations thereof.

In any embodiment, the nanoporous membrane may be bonded to components of the microdevice via one or more second regions of only the first surface.

In any embodiment, the microdevice may have a distance between the bottom surface and the third surface of 1,000 µm or less.

In any embodiment, the first layer and the nanoporous membrane bonded to the top surface may be patterned in a substantially circular shape.

In any embodiment, the sealed chamber may have a volume in the range of $10^2$ to $10^6$ µm$^3$.

In any embodiment, the distance above the third surface may be in the range of 10 nm to 100 µm.

In any embodiment, the first layer may include a first polymeric material.

In any embodiment, the method may further include v) detaching the first layer from the substrate after the removing (iv).

In any embodiment, the method may further include loading the chamber with one or more active agents after the removing (iv). In some embodiments, the active agent is a small molecule, polypeptide, a nucleic acid, or a combination thereof. In some embodiments, the active agent is a hydrophilic agent. In some embodiments, the active agent has a molecular weight of 200 Da or more.

Also provided herein is a method of delivering an active agent to a target tissue, including administering to an individual a composition containing: a therapeutically effective amount of an active agent; and any microdevice of the present disclosure, or a microdevice prepared by any method of the present disclosure, wherein the microdevice is loaded with the active agent. In some embodiments, the chamber of the microdevice comprises the therapeutically effective amount of the active agent. In some embodiments, the active agent is a small molecule, polypeptide, a nucleic acid, or a combination thereof. In some embodiments, the active agent is a hydrophilic agent. In some embodiments, the active agent has a molecular weight of 200 Da or more. In some embodiments, the microdevice is administered orally. In some embodiments, the target tissue is a gastrointestinal tissue.

Kits that include a microdevice of the present disclosure are also provided.

DEFINITIONS

Figure 1A:
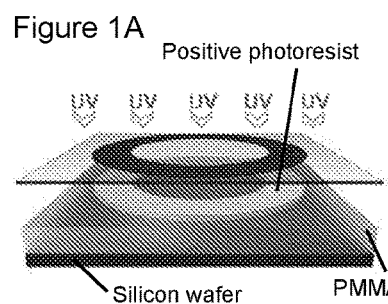
FIGS. 1A-1I are a collection of schematic diagrams showing fabrication of a nanostraw microdevice, according to embodiments of the present disclosure.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

By "small molecule" is meant a non-peptidic, non-oligomeric organic compound that may be synthetic or natural. A small molecule may contain one or more carbon-carbon bonds, and may have a molecular weight of 1500 or less.

"Biocompatible," as used herein, refers to a property of a material that allows for prolonged contact with a tissue in a subject without causing toxicity or significant damage.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in an individual, particularly in a human, and includes: (a) preventing the disease from occurring in an individual which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

"Active agent" and "drug" are used interchangeably to refer to any chemical compound that can have a therapeutic and/or preventive effect for a disease when suitably administered to an individual.

"Therapeutically effective amount" refers to an amount effective, at dosages and for periods of time necessary, to achieve the desired therapeutic result.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

An "individual" as used herein, may be any suitable animal amenable to the methods and techniques described herein, where in some cases, the individual may be a vertebrate animal, including a mammal, bird, reptile, amphibian, etc. The individual may be any suitable mammal, e.g., human, mouse, rat, cat, dog, pig, horse, cow, monkey, non-human primate, etc.

The term "about" as used herein when referring to a measurable value such as an amount, a temporal duration, and the like, is meant to encompass variations of ±20% or ±10%, e.g., ±5%, ±1%, and including ±0.1%, from the specified value, as such variations are appropriate for the disclosed devices or to perform the disclosed methods.

As used herein "substantially", may be applied to modify any quantitative representation that could permissibly vary without resulting in a change in the basic function to which it is related. For example, a fluid-tight chamber may be somewhat permeable to a fluid other than through a nanoporous membrane with which the chamber is bound on one side if the permeability is much greater through the nanoporous membrane compared to other sites and/or there is no measurable fluid exchange other than through the nanoporous membrane during normal use.

"Planar" as used herein, may be applied to modify a three dimensional shape of any object, where the length scale of two dimensions that are substantially perpendicular to each other (e.g., length and width) is longer than the length scale of a third dimension (e.g., thickness) that is substantially perpendicular to both of the other two dimensions. The length scale of one of the two dimensions may be similar to or different from the other dimension. The first two dimensions may define a plane.

"Bound" as used herein, may be applied to describe a physical limit in the spatial extent.

"Interface" as used herein, may describe a boundary surface where distinct physical entities are in direct physical contact with each other. The distinct physical entities may be gaseous, liquid, solid, or any combinations thereof.

"Fluid-tight" as used herein, may be applied to modify the permeability of a fluid through a partition that divides a system into two distinct spaces, where the partition does not permit passage of the fluid there through. In some cases, the partition may define an enclosed space, e.g., a chamber, and an environment external to the enclosed space. In some cases, the partition does not permit passage of the fluid through the partition when the system is under standard temperature and pressure (STP).

"Hydrophilic" as used herein, may describe a molecule or compound that is soluble in water, at least around physiological pH. In some cases, the molecule or compound may have a partition coefficient between water and 1-octanol (log $P_{OW}$) of 1.0 or less, e.g., 0.5 or less, including 0 or less.

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a nanotube" includes a plurality of such nanotubes and reference to "the active agent" includes reference to one or more active agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication by virtue of prior invention. Further, the dates of publication provided may be different from the actual publication dates which may need to be independently confirmed.

DETAILED DESCRIPTION

As summarized above, a microdevice, e.g., a nanostraw microdevice, and methods of fabricating and using the same are provided. As used herein, a microdevice that includes a nanoporous membrane with nanotubes embedded therein, as described herein, may be called interchangeably, a "nanostraw microdevice". The present microdevice may be a multilayered microdevice that includes a chamber having a number of sides, of which one side is bound by a nanoporous membrane layer. The nanoporous membrane may include pores that are formed by hollow nanotubes, e.g., nanostraws, that penetrate the membrane from one side to the other, and the nanotubes may further extend out from the surface of the nanoporous membrane on the surface opposite the surface interfacing the chamber, such that a length at the end of the nanotubes is exposed beyond the surface of the nanoporous membrane. The other layer(s) of the microdevice may form the partitions enclosing the rest of the chamber, and the sides of the chamber other than the nanoporous membrane may not be porous, e.g., not nanoporous. Thus, the chamber is a sealed chamber that is substantially fluid tight other than over the nanoporous membrane, which may provide, via the nanotubes, a fluidic conduit between the chamber and the outside environment.

The nanoporous membrane may be the most superficial layer of the multilayered device, i.e., the nanoporous membrane is bonded to the rest of the microdevice over only one surface of the membrane, whereas the other surface of the nanoporous membrane facing away from the chamber does not interface with other parts of the microdevice, and is exposed to the surrounding environment, extending the exposed ends of the nanotubes therein.

Further aspects of the present microdevices are now described.

Microdevices

Figure 9A:
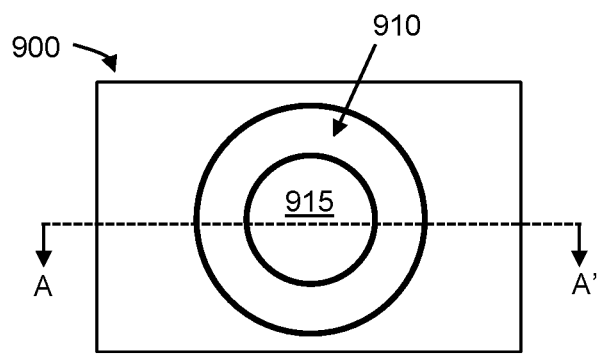
FIGS. 9A-9E are schematic diagrams showing a fabrication method for a microdevice, according to embodiments of the present disclosure.
Figure 9B:
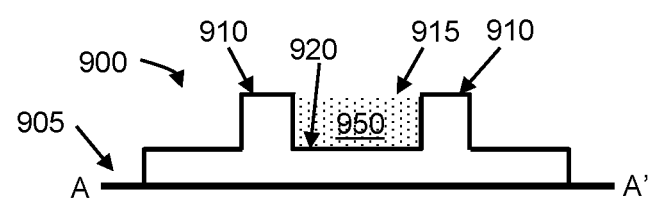
Figure 9C:
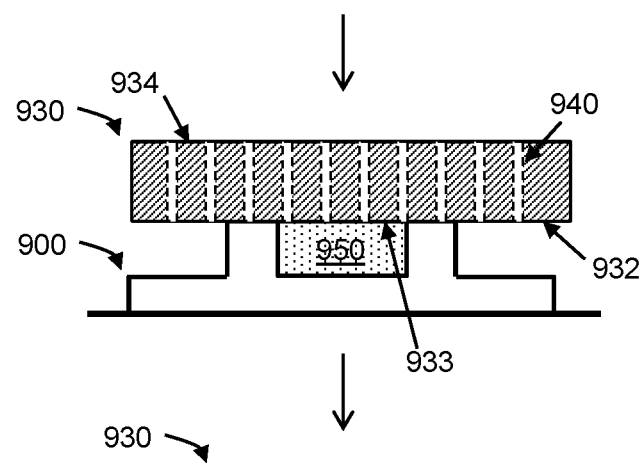
Figure 9D:
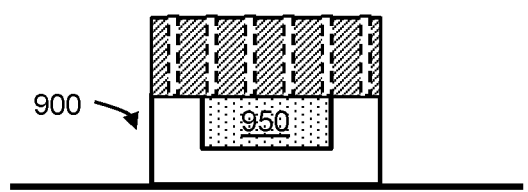
Figure 9E:
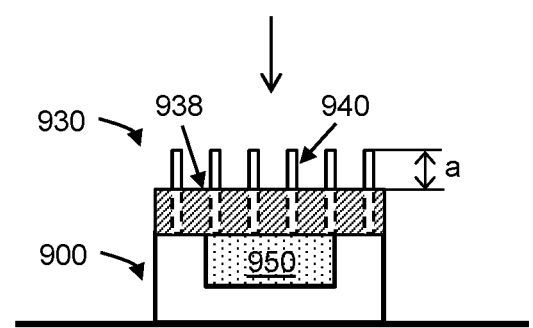

FIG. 9E shows a lateral cut-out view of an embodiment of a microdevice of the present disclosure. The microdevice may include a chamber 950 that is enclosed on one or more sides by a first layer 900 containing partitioning structures. The microdevice includes a nanoporous membrane 930, which includes hollow nanotubes (e.g., nanostraws) 940 that penetrate through the nanoporous membrane, from one surface to the other, and further extends a distance ("a") beyond the surface of the nanoporous membrane 938 opposite the surface interfacing with the chamber. As used herein, the "surface" of the nanoporous membrane refers to a surface defined substantially by the membrane, and may not refer to a surface of the nanotubes.

The nanotubes of the nanoporous membrane may be in fluidic communication with the chamber and with the environment external to the chamber and/or microdevice. Thus when the device is in a fluidic environment, e.g., in a buffer, fluid can diffuse into the chamber through the nanotubes and fill the chamber. Thus, the chamber of the microdevice may be loaded with any agents, e.g., molecules, compounds, and complexes, in the fluid via the nanotubes. The chamber may be substantially fluid-tight such that the nanotubes are the main route for exchange of material, e.g., non-gaseous material, between the chamber and the external environment in a fluid environment under physiological conditions and/or standard temperature and pressure (STP). In some cases the fluidic conduit through the nanotubes may account for 50% or more, e.g., 60% or more, 70% or more, 80% or more, 90% or more, 95% or more, 97% or more, including 99% or more of the exchange of material between the chamber and the external environment. In some cases the fluidic conduit through the nanotubes may account for substantially all the exchange of material between the chamber and the external environment.

The nanoporous membrane 930 is bonded to the rest of the microdevice via a portion of the surface of the membrane that interfaces with the chamber 950, i.e. the surface that is opposite the surface 938 interfacing with the external environment. When the nanoporous membrane is a superficial layer of the microdevice, the nanoporous membrane is bonded to the rest of the microdevice, e.g., the first layer 900, only via a portion of the surface of the nanoporous membrane that interfaces with the chamber, and there is no attachment or bonding at the top surface 938 of the nanoporous membrane to another part, e.g, the first layer, of the microdevice.

The nanoporous membrane 930 may be bonded to the top surface 938 of the first layer 900 using any suitable, biocompatible material. In some embodiments, the nanoporous membrane is bonded to the top surface via a heat-activated, pressure-sensitive adhesive material. Thus, in some cases, the microdevice includes a layer of a heat-activated, pressure-sensitive adhesive material disposed between the nanoporous membrane and the top surface. The heat-activated, pressure-sensitive adhesive material may be any suitable, biocompatible material, including, without limitation, polycaprolactone (PCL), poly-L-lactide (PLLA), poly-DL-lactic acid (DL-PLA), polyglycolic acid (PGA), gelatin, agarose, poly(anhydrides), co-polymers of the above, mixtures of the above, and adducts of the above, or combinations thereof.

The microdevice may have any convenient shape and dimensions. In some cases, the microdevice is a planar device, where the side of the chamber bound by the nanoporous membrane defines a planar surface of the microdevice. The thickness of the microdevice may be defined along the dimension perpendicular to the plane defined by the side of the chamber bound by the nanoporous membrane, and may be measured between the surface of the nanoporous membrane 938 opposite the surface interfacing the chamber, and the bottom surface of the microdevice (e.g., the surface of the microdevice that is most distal to the surface of the nanoporous membrane 938 opposite the surface interfacing the chamber), which may also be the surface contacting the substrate if the substrate is present. Thus, the thickness of the device may not include a length of the nanotubes that extend beyond the surface of the nanoporous membrane 938 opposite the surface interfacing the chamber. In some embodiments, the microdevice has a ratio between a lateral dimension (e.g., a length and/or a width) and a thickness of 2:1 or greater, e.g., 3:1 or greater, 4:1 or greater, 5:1 or greater, 7:1 or greater, 10:1 or greater, 15:1 or greater, including 20:1 or greater, and in some cases a ratio of 1,000:1 or less, e.g., 500:1 or less, 250:1 or less, 100:1 or less, 80:1 or less, 60:1 or less, 40: or less, including 20:1 or less. In some embodiments, the microdevice has a ratio between a lateral dimension (e.g., a length and/or a width) and a thickness in the range of 2:1 to 1,000:1, e.g., 3:1 to 500:1, 4:1 to 250:1, 4:1 to 100:1, 5:1 to 80:1, 5:1 to 60:1, including 5:1 to 40:1.

In some embodiments, the device has a thickness of 1,000 μm or less, e.g., 800 μm or less, 600 μm or less, 400 μm or less, 200 μm or less, 100 μm or less, 80 μm or less, 60 μm or less, 40 μm or less, including 20 μm or less, and in some embodiments, a thickness of 1 μm or more, e.g., 3 μm or more, 5 μm or more, 7 μm or more, 9 μm or more, 12 μm or more, 15 μm or more, including 20 μm or more. In some embodiments, the device has a thickness in the range of 1 to 1,000 μm, e.g., 3 to 800 μm, 5 to 600 μm, 5 to 400 μm, 7 to 200 μm, 9 to 100 μm, 12 to 80 μm, including 15 to 60 μm.

The shape of the microdevice, as observed from the face of the nanoporous membrane, may be, without limitation, circular, oval, square, rectangular, hexagonal, octagonal, pentagonal, a parallelogram, etc. In some cases, the longest lateral dimension of the microdevice (e.g., the diameter of a circular microdevice, the major axis of an oval microdevice, side length of a square, longest side length of a rectangle, longest distance between vortices of an n-sided polygon where n>4, etc.) is 2,000 μm or less, e.g., 1,500 μm or less, 1,000 μm or less, 500 μm or less, 250 μm or less, including 100 μm or less, and in some embodiments, is 10 μm or more, e.g., 20 μm or more, 30 μm or more, 40 μm or more, 50 μm or more, 60 μm or more, 80 μm or more, including 100 μm or more. In some embodiments, the longest lateral dimension of the microdevice is in the range of 10 to 2,000 µm, e.g., 20 to 1,500 µm, 30 to 1,000 µm, 40 to 500 µm, including 50 to 250 µm.

The chamber of the microdevice may have any suitable shape and dimensions. In some cases, the chamber has substantially the same shape as the shape of the microdevice (i.e., the same shape with smaller dimensions). The chamber may have any suitable volume that is bound by the sides. In some cases, the chamber has a volume of $10^2$ µm$^3$ or more, e.g., $10^3$ µm$^3$ or more, $10^4$ µm$^3$ or more, including $10^5$ µm$^3$ or more, and in some cases has a volume of $10^6$ µm$^3$ or less, e.g., $10^5$ µm$^3$ or less, $10^4$ µm$^3$ or less, including $10^3$ µm$^3$ or less. In some cases, the chamber has a volume in the range of $10^2$ to $10^6$ µm$^3$, e.g., $10^3$ to $10^6$ µm$^3$, $10^3$ to $10^5$ µm$^3$, including $10^3$ to $10^4$ µm$^3$.

The first layer 900 of the microdevice containing the partitioning structures may be made of any suitable biocompatible material. In some cases, the chamber 950 is bound by one or more partitioning structures forming the bottom and/or sides of the chamber, where the partitioning structures are made of a biocompatible, polymeric material. The polymeric material may be any suitable biocompatible material for use as the first layer in the present microdevice, including, but not limited to, poly(methyl methacrylate) (PMMA), polydimethylsiloxane (PDMS), polycarbonate (PC), polyethylene terephthalate (PET), chitosan, poly(lactic-co-glycolic acid) (PLGA), poly-2-hydroxyethyl methacrylate (polyHEMA), polystyrene (PS), polyethylene glycol diacrylate-based hydrogels (PEGDA), co-polymers of the above, mixtures of the above, and adducts of the above, or combinations thereof.

Nanoporous Membranes

The nanoporous membrane may be any suitable nanoporous membrane for use in the present microdevices. Suitable nanoporous membranes and methods of making the same are described in, e.g., VanDersarl et al., Nanostraws for direct fluidic intracellular access. *Nano Lett* 2012, 12, 3881-6.

The nanoporous membrane may be made of any suitable biocompatible material for use in the present microdevice. The nanoporous membrane may be made of a material that can be etched. Suitable materials include, without limitation, polycarbonate, polyester, and/or a polymer, that can be processed with pores, silicon, or a combination thereof. In some embodiments, the nanoporous membrane includes polyethylene terephthalate (PET), polylactic acid (PLA), polyglycolic acid (PGA), PLGA, layer-by-layer polyethylene imine/polyacrylic acid, N-isopropylacrylamide (Ni-PAAM), poly(methyl methacrylate) (PMMA), chitosan, protein hydrogels, or a combination thereof.

Nanotubtes of the nanoporous membrane may be made of any suitable material. Suitable biocompatible material for use as nanotubes may be a mechanically stable material that may also have one or more of the following properties: optical transparency, conductance, surface charge state, or chemical reactivity. Suitable materials include, without limitation, alumina ($Al_2O_3$), $TiO_2$, $SnO_2$, $ZrO_2$, $ZnO_2$, carbon, nitrides, platinum, gold, silver, indium tin oxide (ITO), $SiO_2$, Ni, NiO or related transition metals and their corresponding oxides and nitrides, or a combination thereof. In some embodiments, all of the nanotubes can be made of the same material. In some embodiments, a portion of the nanotubes can be made of a first material and a second portion can be made of a second material, where the first a second material are not the same.

The nanotubes may have any suitable inner diameter in the present microdevice, to serve as a fluidic conduit between the chamber and an environment external to the microdevice. In some embodiments, a nanotube has an inner diameter of 5 nm or more, e.g., 10 nm or more, 20 nm or more, 30 nm or more, 40 nm or more, 50 nm or more, 100 nm or more, 200 nm or more, including 400 nm or more, and in some embodiments, has an inner diameter of 1,000 nm or less, e.g., 800 nm or less, 600 nm or less, 500 nm or less, 400 nm or less, 300 nm or less, 200 nm or less, including 100 nm or less. In some embodiments, a nanotube has an inner diameter in the range of 5 to 1,000 nm, e.g., 10 to 800 nm, 20 to 600 nm, 20 to 500 nm, 30 to 400 nm, 30 to 200 nm, including 40 to 100 nm.

The nanotubes may be distributed across the nanoporous membrane in any suitable manner. In some embodiments, the nanotubes are distributed across the nanoporous membrane at a density of $10^6$ cm$^{-2}$ or more, e.g., $2.0 \times 10^6$ cm$^{-2}$ or more, $4.0 \times 10^6$ cm$^{-2}$ or more, $6.0 \times 10^6$ cm$^{-2}$ or more, $8.0 \times 10^6$ cm$^{-2}$ or more, including $10^7$ cm$^{-2}$ or more, and in some embodiments, at a density of $10^{10}$ cm$^{-2}$ or less, e.g., $10^9$ cm$^{-2}$ or less, $5.0 \times 10^8$ cm$^{-2}$ or less, $10^8$ cm$^{-2}$ or less, $8.0 \times 10^7$ cm$^{-2}$ or less, $6.0 \times 10^7$ cm$^{-2}$ or less, $4.0 \times 10^7$ cm$^{-2}$ or less, $2.0 \times 10^7$ cm$^{-2}$ or less, including $10^7$ cm$^{-2}$ or less. In some embodiments, the nanotubes are distributed across the nanoporous membrane at a density in the range of $10^6$ to $10^{10}$ cm$^{-2}$, e.g., $10^6$ to $10^9$ cm$^{-2}$, $10^6$ to $5.0 \times 10^8$ cm$^{-2}$, $10^6$ to $10^8$ cm$^{-2}$, $2.0 \times 10^6$ to $8.0 \times 10^7$ cm$^{-2}$, $4.0 \times 10^6$ to $6.0 \times 10^7$ cm$^{-2}$, $6.0 \times 10^6$ to $8.0 \times 10^7$ cm$^{-2}$, including $8.0 \times 10^6$ to $6.0 \times 10^7$ cm$^{-2}$.

The nanotubes may be distributed across the nanoporous membrane in a substantially random pattern (e.g., where there is no repeated pattern of distribution of the nanotubes across the nanoporous membrane) or in a regular pattern (e.g., distributed in an array, distributed with equal distances between nanotubes, distributed in regular clusters, etc., and combinations thereof).

The distance ("a") beyond which the nanotubes extend over the surface of the nanoporous membrane 938 opposite the surface interfacing with the chamber may be any suitable distance. In some cases, the distance is 10 nm or more, e.g., 100 nm or more, 200 nm or more, 500 nm or more, 1.0 µm or more, 2.0 µm or more, 5.0 µm or more, 10 µm or more, 20 µm or more, including 50 µm or more, and in some cases, is 100 µm or less, e.g., 75 µm or less, 50 µm or less, 25 µm or less, including 10 µm or less. In some embodiments, the distance is in the range of 10 nm to 100 µm, e.g., 100 nm to 75 µm, 200 nm to 50 µm, 500 nm to 25 µm, including 500 nm to 10 µm.

Compositions

Also provided herein are pharmaceutical compositions that include the present microdevice, as described above, and an active agent loaded in the microdevice, e.g., in a chamber of the microdevice, wherein the active agent is present in the composition in a therapeutically effective amount. The therapeutically effective amount may vary, depending on the active agent, the condition to be treated, the dosage form and/or formulation, the dosage regimen, etc.

"Loaded" as used herein, may refer to a configuration of an agent relative to the present microdevice, where the agent is present adsorbed on a surface of the microdevice or is present in the chamber of the microdevice. Where the agent is present in the chamber, the agent may be present in a composition, e.g., a solution, that is insider the chamber, or the agent may be the main component present in the chamber. The chamber may essentially be completely filled with the agent, or a composition containing the agent, or may be partially filled (e.g., 95% or less, 90% or less, 80% or less, 70% or less, 60% or less, 50% or less, 40% or less, 30% or less, 20% or less, 10% or less, 5% or less, 1% or less, down to about 0.1% filled by volume).

The active agent may be present substantially in the chamber of the microdevice and in some cases, may further be adsorbed onto the outer surface of the microdevice (e.g., the surface of the microdevice that does not interface with the chamber.

The active agent may be any suitable agent for delivering to a target site of interest using the present microdevice, as described herein. In some cases, the active agent is a therapeutic agent for treating a condition in an individual by delivering the therapeutic agent using the present microdevice. In some embodiments, the active agent is a small molecule, polypeptide, a nucleic acid, or a combination thereof.

In some cases, the active agent is an anti-cancer agent, such as, without limitation, taxanes (such as paclitaxel or docetaxel); vinca alkaloids, e.g., vinblastine, especially vinblastine sulfate; vincristine, especially vincristine sulfate and vinorelbine; discodermolides; colchicine and epothilones and derivatives thereof, e.g., epothilone B or a derivative thereof; alkylating agents, such as cyclophosphamide, ifosfamide, nitrosourea, temozolomide, or melphalan; 5-fluorouracil (5-FU); capecitabine; gemcitabine; DNA demethylating agents, such as 5-azacytidine and decitabine; methotrexate; edatrexate; and folic acid antagonists; platin compounds, such as carboplatin, cisplatin, cisplatinum, oxaliplatin, satraplatin; topoisomerase I inhibitors, such as camptothecin and derivatives thereof; topoisomerase II, anthracyclines, such as doxorubicin, including liposomal formulation, e.g., caelyx; daunorubicin, including liposomal formulation, e.g., daunosome; epirubicin; idarubicin and nemorubicin; the anthraquinones mitoxantrone and losoxantrone; and the podophillotoxines etoposide and teniposide; VEGF inhibitors; insulin-like growth factor I inhibitors; EGFR kinase inhibitors; mTOR kinase inhibitors; proteasome inhibitors; histone deacteylase (HDAC) inhibitors; etc.

In some embodiments, the active agent is a hydrophilic agent, e.g., hydrophilic compound or molecule. A suitable hydrophilic active agent include, without limitation, insulin, glucagon-like peptide 1, calcitonin, enkephalin, vasopressin, parathyroid hormone, human growth hormone, heparin, enzymes (lipases, esterases, proteases), theophylline, epinephrine, guanoxan, terbutaline, tiacrilast, practolol, atenolol, metoprolol, olsalazine, furosemide, sulpiride, fleroxacin, sulphasalazine, ceftriaxone, etc.

In some embodiments, the active agent has a molecular weight of 200 Da or more, e.g., 500 Da or more, 800 Da or more, 1 KDa or more, 2 KDa or more, 5 KDa or more, including 10 KDa or more, and in some embodiments, a molecular weight of 1,000 KDa or less, e.g., 500 KDa or less, 250 KDa or less, 100 KDa or less, 50 KDa or less, including 40 KDa or less. In some embodiments, the active agent has a molecular weight in the range of 0.2 to 1,000 KDa, e.g., 0.5 to 500 KDa, 1 to 250 KDa, 2 to 100 KDa, including 5 to 100 KDa.

In certain instances, the active agent is a bioactive agent. In some embodiments, the bioactive agent is selected from a polypeptide, growth factor, a steroid, an antibody, an antibody fragment, a DNA, an RNA, and siRNA, an antimicrobial agent, an antibiotic, an antiretro viral drug, an anti-inflammatory compound, an antitumor agent, anti-angiogenic agent, and a chemotherapeutic agent. The bioactive agents may be in a purified form, partially purified form, recombinant form, or any other form appropriate for inclusion in the microdevices. In general, the bioactive agents are free of impurities and contaminants.

Exemplary bioactive agents that may be loaded in the microdevices are sugars, carbohydrates, peptides, nucleic acids, aptamers, small molecules, large molecules, vitamins; inorganic molecules, organic molecules, proteins, co-factors for protein synthesis, antibody therapies, such as Herceptin®, Rituxan®, Myllotarg®, and Erbitux®; hormones, enzymes such as collagenase, peptidases, and oxidases; antitumor agents and chemotherapeutics such as cisplatinum, ifosfamide, methotrexate, and doxorubicin hydrochloride; immuno-suppressants; permeation enhancers such as fatty acid esters including laureate, myristate, and stearate monoesters of polyethylene glycol; bisphosphonates such as alendronate, clodronate, etidronate, ibandronate, (3-amino-1-hydroxypropylidene)-1,1-bisphosphonate (APD), dichloromethylene bisphosphonate, aminobisphosphonatezolendronate, and pamidronate; pain killers and anti-inflammatories such as non-steroidal anti-inflammatory drugs (NSAID) like ketorolac tromethamine, lidocaine hydrochloride, bipivacaine hydrochloride, and ibuprofen; antibiotics and antiretroviral drugs such as tetracycline, vancomycin, cephalosporin, erythromycin, bacitracin, neomycin, penicillin, polymycin B, biomycin, chloromycetin, streptomycin, cefazolin, ampicillin, azactam, tobramycin, clindamycin, gentamicin, and aminoglycocides such as tobramycin and gentamicin; and salts such as strontium salt, fluoride salt, magnesium salt, and sodium salt.

Examples of antimicrobial agents include, but are not limited to, tobramycin, amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, and tioconazole.

Antiangiogenic agents include, but are not limited to, interferon-α, COX-2 inhibitors, integrin antagonists, angiostatin, endostatin, thrombospondin-1, vitaxin, celecoxib, rofecoxib, JTE-522, EMD-121974, and D-2163, FGFR kinase inhibitors, EGFR kinase inhibitors, VEGFR kinase inhibitors, matrix metalloproteinase inhibitors, marmiastat, prinomastat, BMS275291, BAY12-9566, neovastat, rhuMAb VEGF, SU5416, SU6668, ZD6474, CP-547, CP-632, ZD4190, thalidomide and thalidomide analoges, sqalamine, celecoxib, ZD6126, TNP-470, and other angiogenesis inhibitor drugs.

In some embodiments, the bioactive agent is a small molecule, such as, but not limited to, an anti-inflammatory drug, an immunosuppressant drug, a vitamin, micronutrient or antioxidant, an antibacterial drug (e.g., vancomycin or cephazolin), an anti-viral drug (e.g., gancyclovir, acyclovir or foscarnet), an anti-fungal drug (e.g., amphotericin B, fluconazole or voriconazole) or an anti-cancer drug (e.g., cyclophosphamide, ifosfamide, nitrosourea, temozolomide, or melphalan). In some embodiments, the small molecule is a vitamin, micronutrient or antioxidant, such as but not limited to, vitamin A, vitamin C, vitamin E, zinc, copper, lutein or zeaxanthin. In certain embodiments, the small molecule is an immunosuppressant drug, such as but not limited to, cyclosporine, methotrexate or azathioprine. In certain embodiments, the small molecule is an anti-inflammatory drug, such as but not limited to, a corticosteroid (e.g., triamcinolone acetonide or dexamethasone) or a non-steroidal drug (e.g., ketorolac or diclofenac).

In certain embodiments, the large molecule drug is an immunosuppressant drug, such as, but not limited to, etanercept, infliximab or daclizumab. In certain embodiments, the large molecule drug is a neuromuscular blocker drug, such as but not limited to, botulinum toxin A. In certain embodiments, the large molecule drug is a complement inhibitor, such as but not limited to, an anti-C3 compound.

In certain embodiments, the bioactive agent may be Mesalazine, also known as Mesalamine, or 5-aminosalicylic acid (5-ASA), prednisone, TNF inhibitor, azathioprine (Imuran), methotrexate, or 6-mercaptopurine, aminosalicylate anti-inflammatory drugs, corticosteroids, azathioprine, mercaptopurine, methotrexate, infliximab, adalimumab, certolizumab, natalizumab, and hydrocortisone, statins, e.g., atorvastatin, such as atorvastatin calcium, anti-psychotic drugs, e.g., olanzapine.

In certain cases, the bioactive agent may be combined with a pharmaceutically acceptable additive before or after loading of the bioactive agent in a chamber of the present microdevice. The term "pharmaceutically acceptable additive" refers to preservatives, antioxidants, emulsifiers, dyes and excipients known or used in the field of drug formulation and that do not unduly interfere with the effectiveness of the biological activity of the active agent, and that is sufficiently non-toxic to the patient. For example, the bioactive agent may be formulated with inert fillers, anti-irritants, gelling agents, stabilizers, surfactant, emollients, coloring agents, preservatives, or buffering agents, as are known in the art. The term "excipients" is conventionally known to mean carriers, diluents and/or vehicles used in formulating drug compositions effective for the desired use.

A composition containing the present microdevice loaded with an active agent may be provided in a suitable dosage form for administering to an individual, e.g., an individual in need of treatment with the active agent. The dosage form may be in any suitable formulation for administering the microdevice to the individual. Suitable dosage forms include, without limitation, a liquid suspension form, a gel form, a semi-liquid (for example, a liquid, such as a viscous liquid, containing some solid) form, a semi-solid (a solid containing some liquid) form, and/or a solid form, for example. Merely by way of example, a tablet form, a capsule form and/or the like, may be employed.

In some cases, the composition containing a microdevice loaded with an active agent is formulated into an oral, or intranasal dosage forms. Oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated.

In one embodiment, the pharmaceutical composition is contained in capsules. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the pharmaceutical composition for oral use can be obtained by mixing the microdevice loaded with an active agent with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For buccal administration, the pharmaceutical composition may take the form of tablets or lozenges formulated in a conventional manner.

The preparation of pharmaceutical compositions of the present disclosure is conducted in accordance with generally accepted procedures for the preparation of pharmaceutical preparations. See, for example, *Remington's Pharmaceutical Sciences* 18*th Edition* (1990), E. W. Martin ed., Mack Publishing Co., PA.

Alternative formulations include formulations for other routes of administration, including, without limitation, parenteral administration (e.g., transcutaneous, transdermal, intravenous, intramuscular, subdermal administration, etc.).

Methods

Also provided herein is a method of preparing a microdevice, as described above. The present microdevice may be a multilayered microdevice that is prepared by depositing layers of material components of the microdevice in a controlled manner (e.g., by controlled deposition and/or controlled patterning), to form the chamber bound on one side by a nanoporous membrane. An embodiment of the present method may be described with respect to FIGS. 9A-9E.

With respect to FIGS. 9A and 9B, the present method may include fabricating a first layer 900, e.g., a PMMA layer, that includes a bottom surface 920 of a chamber 950 and one or more lateral partitions of the chamber (FIG. 9B). The exposed end of the lateral partition that is distal to the bottom surface may be described as the top surface 910 of the first layer, which top surface may circumscribe an opening 915 of the chamber (FIG. 9A, showing a top view of the first layer). Thus, the first layer may form an open chamber with an opening at one end. The first layer may be fabricated on a substrate 905.

The first layer 900 may be fabricated using any suitable method. In some cases, the first layer is fabricated by depositing a base layer on the substrate 905, where the base layer is of a material that can be etched, e.g., by reactive ion etching (RIE). A protective layer, e.g., a photoresist, may be deposited over the base layer, the protective layer may be exposed to a patterning stimulus, e.g., ultraviolet (UV) light, through a mask, e.g., a photomask, so that the protective layer overlies regions of the base layer that will eventually provide the top surface 910 of the first layer 900. If the photoresist is a negative photoresist, the photomask exposes regions of the base layer that are to be protected from the etching, and if the photoresist is a positive photoresist, the photomask covers regions of the base layer that are to be protected from the etching. The base layer is then patterned, e.g., by anisotropic RIE with oxygen, to form the first layer.

The top surface 910 of the first layer 900 may then be bonded with a nanoporous membrane 930, e.g., a track-etched polycarbonate (PC) with interspersed aluminum oxide nanotubes, so that a fluid-tight seal is formed between the top surface and the nanoporous membrane (FIG. 9C). The nanoporous membrane includes a first surface 932 containing a first region 933 that interfaces with the chamber 950, a second surface 934 opposite the first surface, and hollow nanotubes 940 that are embedded in and extend through the nanoporous membrane, from the first surface to the second surface.

Once the nanoporous membrane 930 is bonded to the top surface 910 of the first layer 900, the nanoporous membrane and the first layer may be patterned to a desired dimension, e.g., by reactive ion etching (RIE) (FIG. 9D). The nanoporous membrane and the first layer may be patterned using any suitable method. In some cases, the nanoporous membrane and the first layer are patterned by anisotropic RIE with, e.g., oxygen. In some cases, the patterning includes depositing a sacrificial layer, e.g., a layer of poly(vinyl alcohol) over the nanoporous membrane, depositing a protective layer over the sacrificial layer in a pattern of interest, patterning the nanoporous membrane and the first layer using RIE with, e.g., oxygen. The patterning of the nanoporous membrane and the first layer using RIE may further include exposing the protective layer to a patterning stimulus, e.g., ultraviolet (UV) light, through a mask, e.g., a photomask, so that the protective layer overlies regions of the sacrificial layer in a pattern of interest, and anisotropically etching the nanoporous membrane and the first layer using RIE. If the photoresist is a negative photoresist, the photomask exposes regions of the sacrificial layer that are to be protected from the etching, and if the photoresist is a positive photoresist, the photomask covers regions of the sacrificial layer that are to be protected from the etching.

In some cases, all the nanoporous membrane and the first layer that surround the microdevice are removed by the patterning. In some cases, a plurality of microdevices are prepared on a substrate using a method as described herein, and the patterning of the nanoporous membrane and the first layer separates each microdevice from one another.

After patterning the nanoporous membrane and the first layer, a sublayer of the nanoporous membrane 930 may be removed from the top, e.g., by low-energy RIE, to expose a third surface 938 of the nanoporous membrane, without removing corresponding sections of the nanotubes so that the nanotubes 940 extend beyond a distance ("a") above the third surface (FIG. 9E). The sealed chamber may be fluid-tight, except for the nanotubes of the nanoporous membrane that provide for a fluidic conduit between the chamber 950 and the external environment, as described above.

The nanoporous membrane 930 may be bonded to the top surface 910 of the first layer 900 using any suitable method that produces a fluid-tight contact between the nanoporous membrane and top surface. In some cases, the bonding includes depositing a second layer of a heat-activated, pressure-sensitive adhesive, e.g., polycaprolactone (PCL), on the top surface, and heat bonding the nanoporous membrane to the top surface.

In some cases, where the nanoporous membrane 930 is the most superficial layer of the multilayered microdevice, the nanoporous membrane is bonded to the rest of the microdevice through regions of the first surface 932 only (i.e., there is no contact or bonding interaction between the second surface 934 of the nanoporous membrane and other components of the microdevice.

The present microdevice may have any suitable shape and dimensions, as described above. In some cases, the first layer 900 and the nanoporous membrane 930 of the present microdevice are configured such that a distance between the bottom surface 920 of the chamber and the third surface 938 of the nanoporous membrane is 5 µm or more, e.g., 8 µm or more, 10 µm or more, 12 µm or more, 15 µm or more, 20 µm or more, including 30 µm or more, and in some cases the distance is 1,000 µm or less, e.g., 500 µm or less, 200 µm or less, 100 µm or less, 80 µm or less, 60 µm or less, 40 µm or less, including 20 µm or less. In some cases, the first layer 900 and the nanoporous membrane 930 of the present microdevice are configured such that a distance between the bottom surface 920 of the chamber and the third surface 938 of the nanoporous membrane is in the range of 5 to 1,000 µm, e.g., 8 to 500 µm, 10 to 200 µm, 10 to 100 µm, 12 to 80 µm, including 15 to 40 µm.

The nanoporous membrane 930 and the first layer 900 may be patterned to any convenient shape, including, but not limited to, a circular, oval, square, rectangular, hexagonal, octagonal, pentagonal, a parallelogram, etc, shape, as seen from the surface of the nanoporous membrane.

The nanoporous membrane may be any suitable nanoporous membrane, as described above. The nanoporous membrane may be fabricated using any suitable method, as described in, e.g., VanDersarl et al., Nanostraws for direct fluidic intracellular access. *Nano Lett* 2012, 12, 3881-6.

The substrate 905 may be any suitable substrate. In some cases, the substrate is a silicon substrate, e.g., a silicon wafer.

In some embodiments, the present method further includes detaching the first layer 900 from the substrate 905 after removing a sublayer of the nanoporous membrane 930 to expose the third surface 938 and the nanotubes 940, thereby releasing the microdevice from the substrate. The detaching may be done using any suitable method. In some cases, the detaching includes scraping the substrate with a sharp edge, e.g., a razor blade.

In some embodiments, the method includes loading the chamber 950 with one or more active agents after removing a sublayer of the nanoporous membrane 930 to expose the third surface 938 and the nanotubes 940. The active agent may be any suitable agent for delivering to a target site of interest using the present microdevice, as described above.

The loading may be done using any suitable method. In some cases, the loading includes submerging the microdevice in a solution containing an amount of the active agent to form a combination, and incubating the combination for a length of time. The incubation time may be any suitable length of time, and may be 1 hr or longer, e.g., 2 hrs or longer, 3 hrs or longer, 5 hrs or longer, 10 hrs or longer, 16 hours or longer, 24 hrs or longer, 2 days or longer, including 3 days or longer, and in some cases, may be 1 year or less, e.g., 6 months or less, 3 months or less, 1 month or less, 2 weeks or less, 1 week or less, 5 days or less, including 2 days or less. In some embodiments, the microdevice may be incubated with a solution containing the active agent for a time in the range of 1 hr to 1 year, e.g., 2 hrs to 6 months, 3 hrs to 3 months, 5 hrs to 1 month, 10 hrs to 2 weeks, 10 hrs to 1 week, 10 hrs to 5 days, including 16 hrs to 2 days.

Utility

The present microdevices find use as a vehicle for delivering active agents, e.g., pharmaceutical drugs, to a target site of interest, e.g., the gastrointestinal (GI) tract. The nanotubes of the microdevice provides for a conduit for loading active agents by diffusion into the microdevice chamber. Inside the chamber, the active agent may be stored in concentrated form and may be protected from degrading enzymes in the environment, such as the GI tract.

Thus, the present disclosure provides for a method including administering to an individual a composition that includes a therapeutically effective amount of an active agent, and a microdevice, as described herein, loaded with the active agent. The microdevice may be administered using any suitable method, and the administration may depend on the dosage form of the composition, as described above. In some cases, the administering includes administering the composition orally, e.g., when the composition is an oral dosage form. Any other suitable routes of administration may be employed, including, but not limited to nasal, anal, vaginal, transcutaneous, surgical routes, etc.

The target site may be any suitable target tissue. In some cases, the target tissue includes the gastrointestinal (GI) tract. In some cases, the target tissue is the buccal cavity, the stomach, the intestine, the rectum, etc. The active agent may be any suitable active agent, as described above.

The present microdevice may provide for enhanced adhesion to a target tissue and deliver an active agent loaded therein to the target tissue without detaching from the target tissue due to shear stress. In some cases, the present microdevice can withstand detachment under higher level of fluid shear stress than a comparable microdevice that does not contain nanotubes that extend from the surface of the nanoporous membrane. In some cases, the present microdevice can withstand detachment under fluid shear stress of 1 $dyn/cm^2$ or more, e.g., 2 $dyn/cm^2$ or more, 5 $dyn/cm^2$ or more, 10 $dyn/cm^2$ or more, 20 $dyn/cm^2$ or more, including 30 $dyn/cm^2$ or more, and in some cases under fluid shear stress of 100 $dyn/cm^2$ or less, e.g., 75 $dyn/cm^2$ or less, 50 $dyn/cm^2$ or less, including 40 $dyn/cm^2$ or less. In some cases, the present microdevice can withstand detachment under fluid shear stress in the range of 1 to 100 $dyn/cm^2$, e.g., 2 to 75 $dyn/cm^2$, 5 to 50 $dyn/cm^2$, including 10 to 40 $dyn/cm^2$. Resistance to detachment under fluid shear stress may be measured, e.g., by attaching the microdevice to a monolayer of epithelial cells, exposing the attached microdevice to a flow having the appropriate shear stress value for 5 minutes, and measuring the fraction of microdevices remaining attached to the monolayer. In some cases, a fraction of greater than 75% may indicate resistance to detachment. In some cases, the resistance to detachment may be determined relative to an appropriate control, e.g., a comparable microdevice that does not contain nanotubes that extend from the surface of the nanoporous membrane.

The present microdevice may provide for a controlled release vehicle for delivering an active agent, e.g., insulin, loaded in the microdevice. The active agent release rate may be controlled, e.g., by adjusting the density of the nanotubes in the nanoporous membrane, and/or adjusting the inner diameter of the nanotubes.

The present microdevice may provide for delivery of an active agent that is stable and/or resistant to degradation at and/or on the way to a target tissue. In some embodiments, the present microdevice slows entry of a digestive enzyme in a target tissue, from an environment exterior to the microdevice into the chamber, such that the digestive enzyme achieves 50% or less, e.g., 40% or less, 30% or less, 25% or less, including 20% or less saturation of the chamber in 30 minutes or more, e.g., 1 hr or more, 1.5 hrs or more, 2 hrs or more, 3 hrs or more, and up to 4 hours.

Kits

Also provided herein is a kit that includes a microdevice, as described herein, and a packaging material (e.g., a vial, a blister packaging, a tube, a bag, a box, etc.) configured to hold the microdevice. In some cases, the packaging is a sterile packaging. In some cases, the microdevice is part of a composition, as described herein, and the packaging is configured to hold the composition.

In some embodiments, a microdevice of the present kit is loaded with an active agent, i.e., the chamber of the microdevice contains the active agent. In some embodiments, the kit contains an active agent as a separate component from the microdevice.

In some embodiments, the present kit includes instructions for using a microdevice of the present disclosure, e.g., for delivering an active agent to a target tissue of interest and/or loading the microdevice with the active agent. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

Components of a subject kit can be in separate containers; or can be combined in a single container.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Methods and Materials

The following methods and materials were used in the Examples.

Fabrication of Nanostraw Microdevices.

Unless otherwise noted, all materials were purchased from Sigma-Aldrich (St. Louis, Mo.). All spin casting steps were performed for 30 s following a 10 s pre-spin at 350-500 rpm. First, two layers of 110 mg/mL 950 kDa poly(methyl methacrylate) (PMMA) (MicroChem) in anisole were deposited onto a 3-inch-diameter <111> silicon wafer (Addison Engineering) by spin casting at 1350 rpm and baking at 110° C. for 1 min. Microposit S1818 photoresist (MicroChem) was spun cast over the PMMA at 2500 rpm and baked at 110° C. for 1 min. The photoresist was exposed to 225 mJ/cm$^2$ of UV light through a computer-designed photomask with arrays of opaque annuli (200 µm outer diameters, 100 µm inner diameters, 400 µm pitch). The photoresist was submerged in 351 Developer (MicroChem) diluted 1:3 in distilled water (dH$_2$O) for 2 min under gentle shaking. The 8 µm PMMA layer was anisotropically etched 5.5 µm in regions not protected by photoresist by reactive ion etching with oxygen (450 W, 250 mTorr, 6.5 min). The remaining photoresist was removed by submerging in Microposit Remover 1112A (MicroChem) for 2 min and then rinsing with dH$_2$O. A wafer previously spun cast with 75 mg/mL 80 kDa polycaprolactone (PCL) in trifluoroethanol at 1750 rpm was brought into contact with the microdevices on a hot plate at 80° C., and the wafers were quickly separated. Nanostraw membranes were fabricated as previously described,[1] with minor modifications. Briefly, track-etch polycarbonate membranes (GVS, Sanford, Me.) with varying pore diameters and densities were coated with aluminum oxide by atomic layer deposition, and the aluminum oxide layer was anisotropically etched by RIE with BCl$_3$ (60 W, 5 mTorr, 5 min) on both sides of the membrane, waiting until the final fabrication step to expose the nanostraws by etching polycarbonate (PC) by reactive ion etching (RIE) with oxygen. The membrane was then brought into contact with the microdevices at 80° C., melting the PCL and bonding the membrane to the devices. The membrane was spun cast with two layers of 75 mg/mL poly(vinyl alcohol) (PVA) at 2500 rpm, curing at 95° C. for 1 min after each deposition. SU-8 2015 (MicroChem) was then spun cast at 1250 rpm and cured at 95° C. for 5 min. The SU-8 was exposed to 250 mJ/cm$^2$ of ultraviolet (UV) light through an opaque photomask with 200 µm transparent circles aligned to the microdevices and then baked at 95° C. for 5 min. The devices were submerged in SU-8 Developer (MicroChem) for 5 min under gentle shaking and dried with a nitrogen gun. The membrane overhang and remaining PMMA between microdevices was removed by RIE with oxygen (450 W, 250 mTorr, 40 min). The devices were rinsed in dH$_2$O, dissolving the PVA and allowing the SU-8 caps to detach. The nanostraws were then exposed by partially etching the surrounding polycarbonate by RIE with oxygen at a lower energy (100 W, 250 mTorr, 20 min).

Device Profilometry.

Device height profiles were measured with an Ambios XP2 profilometer at various fabrication steps to determine nanostraw microdevice dimensions. Specifically, the height profiles of devices with etched PMMA after removal of photoresist, etched PMMA coated with PCL, and complete devices were measured over the center of the devices. The thicknesses of the nanostraw membrane (following etching to expose nanostraws) and the PMMA base layer were also measured via profilometry. The PMMA base layer was scratched to expose the underlying silicon wafer prior to measurement. To account for the thickness of PMMA to be etched in remaining fabrication steps, the thickness of the PMMA base layer was added to the height profiles of the etched PMMA devices and the etched PMMA devices coated with PCL. The profile of the base of the nanostraw membrane was determined by subtracting the thickness of the nanostraw membrane from the profile of complete devices.

Scanning Electron Microscopy (SEM).

Samples were sputter-coated with 8 nm of gold or iridium and imaged with a Carl Zeiss Ultra 55 Field Emission Scanning Electron Microscope. Nanostraw diameters were measured to be 62±3, 94±5, 165±9, (membranes with nanostraw densities of 10$^7$ cm$^{-2}$) and 86±17 nm (membrane with a nanostraw density of 3×10$^7$ cm$^{-2}$) by analyzing SEM images with FIJI software.

Confocal Imaging.

Devices were incubated in 10 mg/mL fluorescein isothiocyanate (FITC)-bovine serum albumin (BSA) (Sigma-Aldrich) in phosphate buffer saline (PBS) overnight, incubated in PBS at 37° C. for approximately 8 hours, and imaged in PBS (pH 7.4) with a spectral confocal microscope with a 488 nm laser for excitation and a 525 nm emission filter. Z-stacks were captured at 1 µm intervals over the entire device structure. FIJI software was used to restack confocal images along the z-axis.

Reservoir Seal Integrity Assay.

Devices fabricated using a nanostraw membrane (inner nanostraw diameter: 60 nm, nanostraw density: 10$^7$ cm$^{-2}$) or with a non-porous PC membrane were incubated in 10 mg/mL FITC-insulin in PBS (Sigma-Aldrich) overnight, and rinsed with PBS. Devices were then submerged in PBS and imaged with brightfield microscopy to show device structure and fluorescence microscopy to determine FITC-insulin uptake.

Flow Cell Adhesion Assay.

An epithelial adhesion flow cell assay was performed as previously outlined (Fischer et al., Biomimetic nanowire coatings for next generation adhesive drug delivery systems. *Nano Lett* 2009, 9, 716-20) with minor modifications. Briefly, approximately 400 microdevices, with or without the final RIE step to expose nanostraws (inner diameter: 60 nm, density: 10$^7$ cm$^{-2}$), were scraped from the silicon wafer with a razor, suspended in 1 mL PBS, and added to a monolayer of Caco-2 epithelial cells (ATCC) in a petri dish. The devices were incubated over the cellular monolayer for 5 min under gentle shaking. A flow cell was then assembled over the devices, and a solution of 20 g/L porcine mucin (Sigma-Aldrich) in PBS was passed through the flow cell at increasing flow rates in a stepwise fashion, achieving fluid shear stress values of 0.5, 1, 5, 10, 20, and 40 dyn/cm$^2$. After 5 min at each flow rate, the number of completely adhered devices (i.e., the number of devices lying flat on the Caco-2 monolayer) was determined by counting under a dissecting microscope, and the ratio of devices adhered to the original number of devices was determined.

Drug release assay. Silicon wafers with nanostraw microdevices were scored and broken into pieces approximately 1 to 2 cm$^2$ in area, and the devices on each piece were counted. The devices were then incubated in a PBS solution of 10 mg/mL FITC-insulin at 4° C. for 36-48 hours, rinsed in PBS for 1 min to rinse non-loaded FITC-insulin from the devices, and placed in a PBS solution at 37° C. The PBS solution was sampled with complete buffer exchange at 0.25, 0.5, 1, 2, and 4 hours. Drug concentrations were determined with fluorescence spectroscopy using a standard curve of serially diluted FITC-insulin, and the mass of released drug was normalized to device count.

Testing Nanostraw Microdevice Retention of Drug Following Removal of Devices from the Silicon Wafer.

Devices were incubated in a PBS solution of 10 mg/mL FITC-insulin overnight, rinsed with PBS, and scraped from the wafer with a razor. Devices were then loaded into a 1.5×24×0.12 mm channel formed by placing an adhesive spacer (Grace Bio-labs) between a glass slide and coverslip.

The devices were then incubated at room temperature for 30 min and then imaged with brightfield and fluorescence microscopy.

Quantification of FITC-Dextran Permeation.

Nanostraw microdevices were incubated in a PBS solution of 1 mg/mL 10 kDa FITC-dextran (Sigma-Aldrich) at 37° C. At 0, 0.5, 1, 2, 4, and 48 hours, devices were quickly rinsed in PBS and imaged with confocal fluorescence microscopy, imaging with 2 µm z-steps over the entire device reservoirs. All samples were imaged under identical conditions while avoiding saturation of fluorescence signal. The fluorescence intensity within device reservoirs was integrated for each timepoint with FIJI software, subtracting background fluorescence intensity determined by 0 h samples. Percent of maximum fluorescence intensity was quantified as the ratio of fluorescence intensity at each timepoint to fluorescence intensity of devices saturated with FITC-dextran by incubation for 48 hours.

Example 2: Fabrication of Sealed Nanostraw Microdevices for Oral Drug Delivery

Figure 1D:
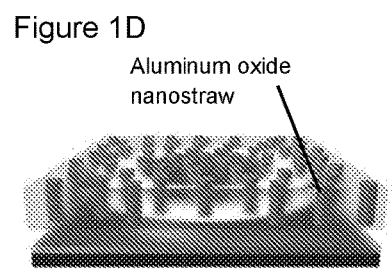
Figure 1G:
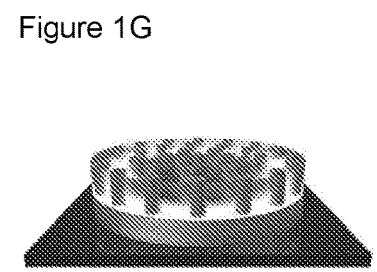
Figure 1B:
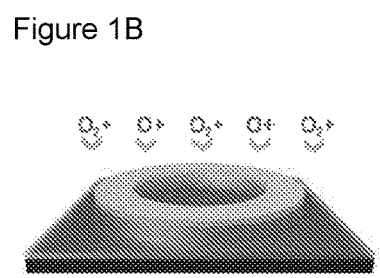
Figure 1E:
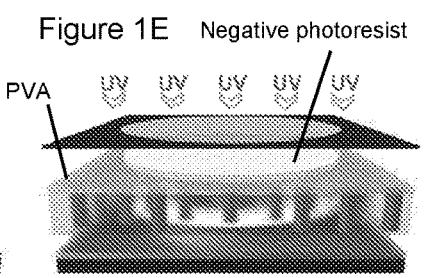
Figure 1H:
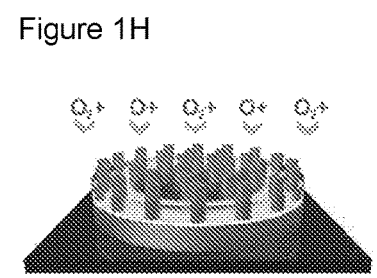
Figure 1C:
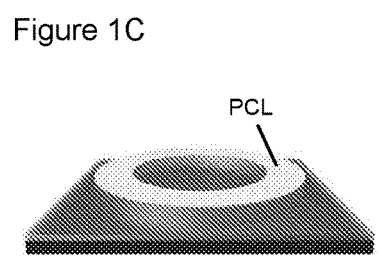
Figure 1F:
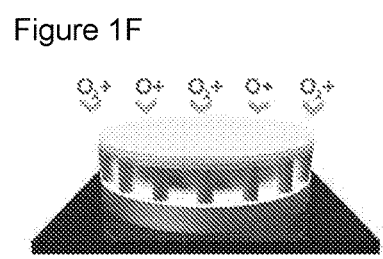
Figure 1I:
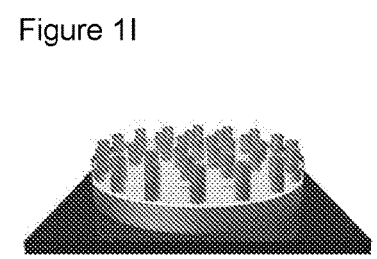

Devices were designed to have circular bodies 200 µm in diameter with 100-µm-diameter drug reservoirs sealed by nanostraw membrane caps, with a total device thickness <20 µm to retain a planar, asymmetric microdevice design. The devices were fabricated through a series of deposition, photolithography, and anisotropic etching steps as shown in FIGS. 1A-1I. First, an 8-µm-thick layer of poly(methyl methacrylate) (PMMA) followed by a layer of positive photoresist were spun cast onto a silicon wafer. The device body was then defined by exposing with UV light through a computer-designed photomask with arrays of opaque annuli (200 µm outer diameter, 100 µm inner diameter, 400 µm pitch) and subsequently developing the photoresist (FIG. 1A). The PMMA was anisotropically etched approximately 5.5 µm in regions not protected by patterned photoresist (FIG. 7) by reactive ion etching (RIE) with oxygen (FIG. 1B). The remaining photoresist was chemically stripped, and the devices were brought into contact with a polycaprolactone (PCL) film under heat, coating the topmost surface of the PMMA device bodies with a layer of PCL (FIG. 1C). To seal the device reservoirs, a nanostraw membrane composed of track-etched polycarbonate (PC) with interspersed aluminum oxide nanostraws was fabricated as previously described (VanDersarl et al., Nanostraws for direct fluidic intracellular access. Nano Lett 2012, 12, 3881-6) and heat-bonded to the PCL (FIG. 1D). To protect the nanostraw membrane during subsequent lithography steps, a sacrificial poly(vinyl alcohol) (PVA) layer was spun cast over the nanostraw membrane. A negative photoresist was spun cast over the PVA. The photoresist was then crosslinked in regions covering the devices by UV exposure through an aligned photomask with subsequent dissolution of non-crosslinked regions in developer (FIG. 1E). The membrane and remaining PMMA between devices was removed via RIE with oxygen (FIG. 1F), and the devices were rinsed in water to dissolve the PVA and release the photoresist caps (FIG. 1G). The devices were then exposed to low-energy RIE with oxygen to partially etch the PC, exposing the nanostraws (FIG. 1H). Finally, the devices were incubated in concentrated drug solutions to load the device reservoirs via diffusion through nanostraws (FIG. 1I). The final nanostraw microdevices were composed of PMMA, PCL, PC, and aluminum oxide, which are FDA-approved materials in various implanted biomedical devices.

FIGS. 1A-1I. Nanostraw Microdevice Fabrication Schematic.

FIG. 1A. A silicon wafer is spun cast with 1) PMMA and 2) positive photoresist, and the photoresist is patterned via UV exposure through a computer-designed photomask with subsequent development. FIG. 1B. The PMMA layer is partially etched via RIE with oxygen to form the device body. FIG. 1C. Following chemical removal of remaining photoresist, PCL is transferred onto the surface of the devices by contact under heat. FIG. 1D. The devices are heat-bonded to a nanostraw membrane composed of PC (semi-transparent) interspersed with aluminum oxide nanostraws, sealing the devices. FIG. 1E. The membrane is spun cast with 1) PVA and 2) negative photoresist, which is patterned over the devices via UV exposure through a photomask with subsequent development. FIG. 1F. RIE is used to etch away the membrane and remaining PMMA in regions not protected by the patterned photoresist. FIG. 1G. The photoresist caps are removed by dissolving the underlying PVA layer in water. FIG. 1H. RIE is used to partially etch through polycarbonate to expose the alumina nanostraws. FIG. 1I. The devices are submerged in a concentrated solution of drug, facilitating nanostraw-mediated diffusion of drug into device reservoirs.

Figure 7:
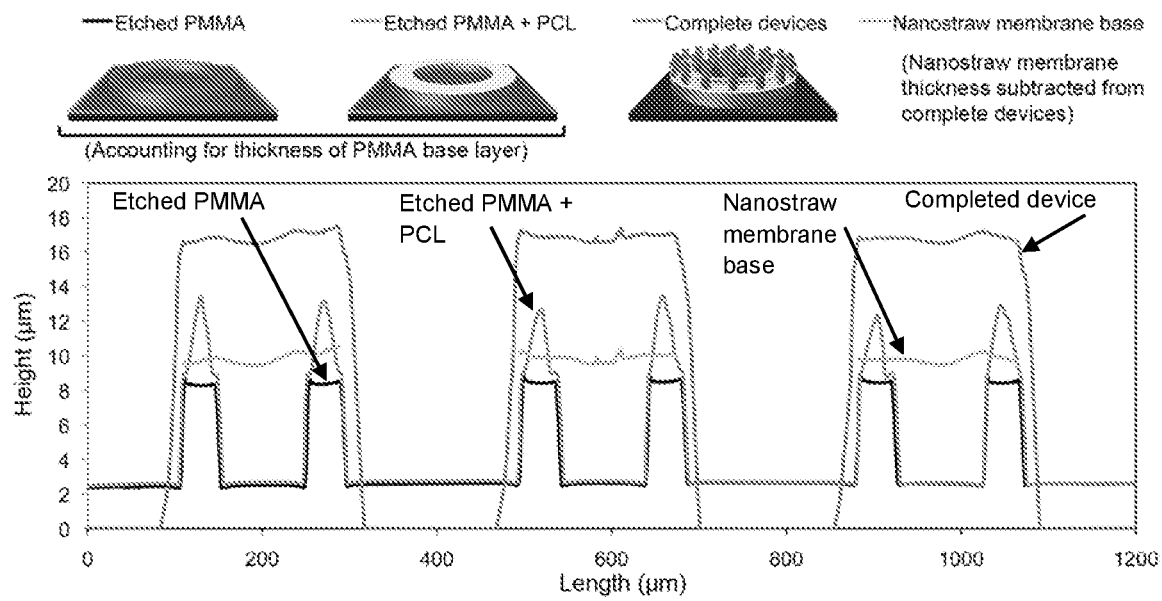
FIG. 7 is a collection of schematic diagrams and graphs showing the height profiles of microdevices at various stages of fabrication, according to embodiments of the present disclosure.

FIG. 7. Height Profiles of Microdevices at Various Stages of Fabrication.

Height profiles show thicknesses of approximately 2.5 µm for the PMMA base layer, 7.5 µm for drug reservoirs, 7 µm for nanostraw membranes (following etching to expose nanostraws), and 17 µm for total device thickness (not accounting for nanostraw length). PCL thickness was 5 µm before nanostraw membrane bonding and 1-2 µm following compression during bonding.

Figure 2A:
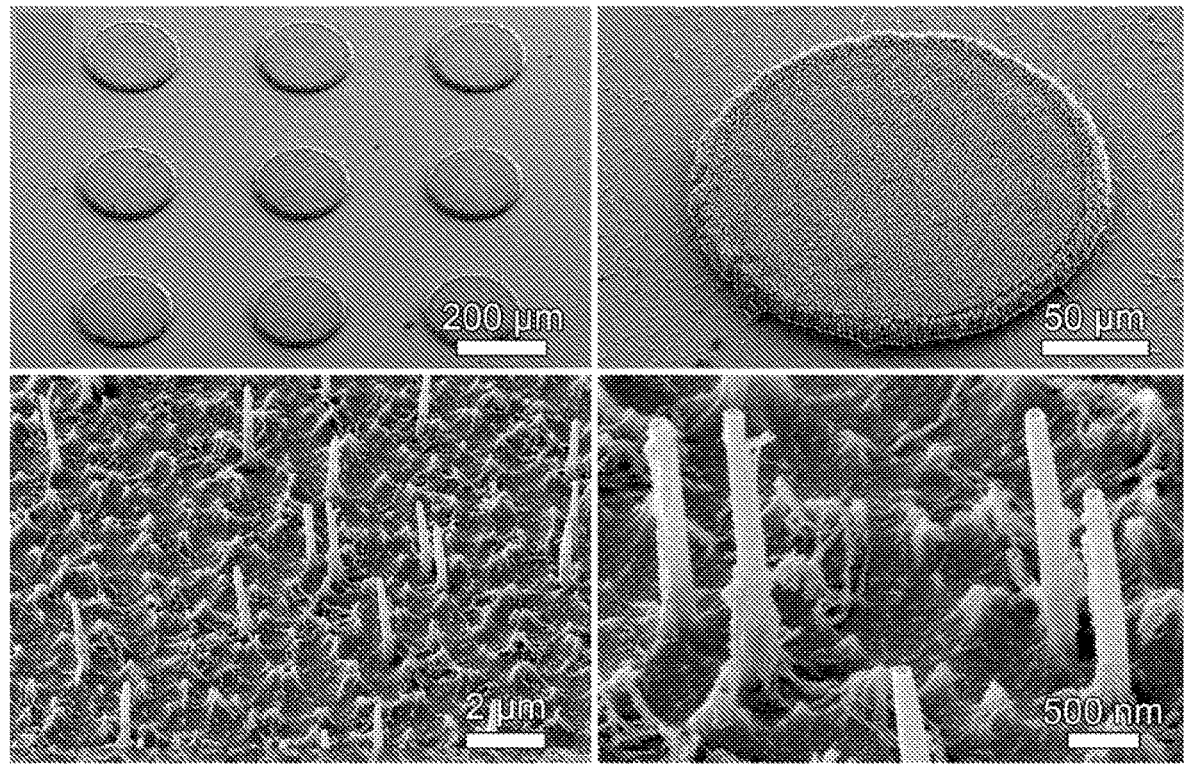
FIGS. 2A-2B are a collection of images showing the structure of nanostraw microdevices, according to embodiments of the present disclosure.
Figure 2B:
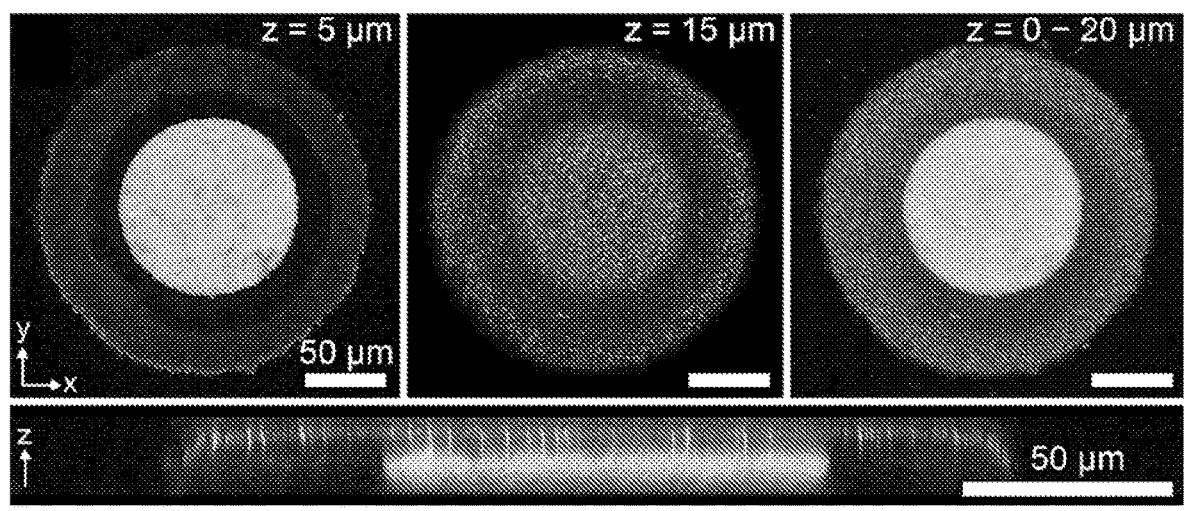

Scanning electron microscopy (SEM) demonstrated that nanostraw membrane caps had bound to the underlying PMMA device bodies (FIG. 2A). The membranes had intact nanostraws measuring 2.2±0.1 µm in length. To characterize internal structure, microdevices were incubated in FITC-tagged bovine serum albumin (FITC-BSA) overnight, allowing the fluorescently labeled BSA to both diffuse into device reservoirs and adsorb onto the surfaces of the devices. The devices were then incubated in phosphate buffered saline (PBS) and imaged with confocal fluorescence microscopy. Z-slices of different depths showed the presence of drug reservoirs 100 µm in diameter with a surrounding device body and an overlying nanostraw membrane, both 200 µm in diameter (FIG. 2B). Cross-sections restacked along the z-axis showed that nanostraws spanned through the membrane cap, connecting the device reservoirs to the external environment. Together, these findings indicated that loading of the reservoirs was mediated by diffusion of drug through the nanostraws.

FIGS. 2A-2B. Characterization of Nanostraw Microdevices Structure.

FIG. 2A. SEM images demonstrate that microdevices were fabricated with intact nanostraw membranes. FIG. 2B. Confocal fluorescence microscopy of nanostraw devices incubated in a FITC-BSA solution and imaged while submerged in PBS provides visualization of the drug reservoir (z=5 µm), the overlying nanostraw membrane (z=15 µm), and overall device structure (z=0-20 µm). A cross-section restacked along the z-axis shows that nanostraws provide a pipeline between device reservoirs and the external environment.

To validate the integrity of device sealing and confirm nanostraws as the route of drug diffusion into the device reservoirs, devices with either nanostraw membrane caps or non-porous PC film caps as a control were fabricated. Devices were then incubated overnight in a PBS solution of 10 mg/mL FITC-insulin, rinsed with PBS for 1 min, and imaged with fluorescence microscopy. FITC-insulin diffused into the reservoirs of devices with nanostraw membranes but not into reservoirs of devices sealed with non-porous PC (FIGS. 3A-3B), demonstrating functional device reservoir sealing with drug diffusion occurring primarily through nanostraws. Additionally, drug-loaded devices retained FITC-insulin upon being scraped from the silicon wafer (FIG. 8), indicating that the device seals remained intact upon device removal.

Figure 3A:
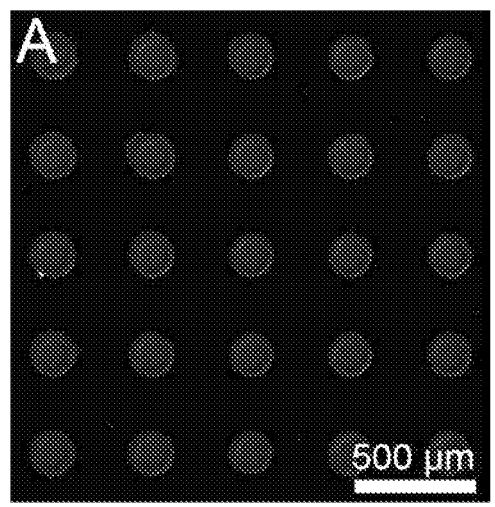
FIGS. 3A-3B are a collection of images showing that nanostraw microdevices are sealed and that the nanostraws facilitate in-solution drug loading, according to embodiments of the present disclosure.
Figure 3B:
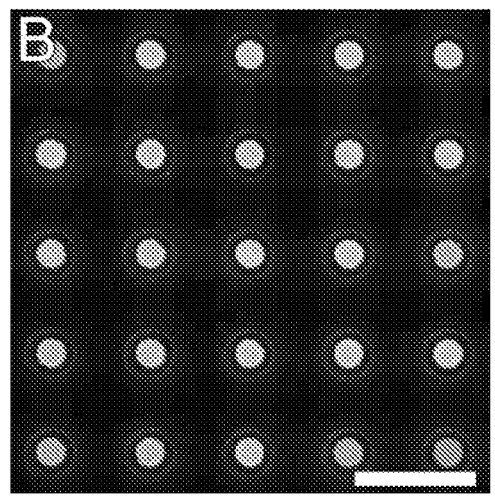

FIGS. 3A-3B. Nanostraw Microdevice Reservoirs are Sealed, with Nanostraws Facilitating in-Solution Drug Loading.

Microdevices fabricated using a non-porous PC membrane (FIG. 3A) or a nanostraw membrane (FIG. 3B) were incubated in 10 mg/mL FITC-insulin overnight, rinsed with PBS, and imaged for device structure (brightfield signal) and FITC-insulin localization (fluorescence signal) while submerged in PBS. Only devices with nanostraws showed significant uptake of insulin into reservoirs, indicating proper sealing of devices with drug diffusion occurring primarily through nanostraws.

Figure 8:
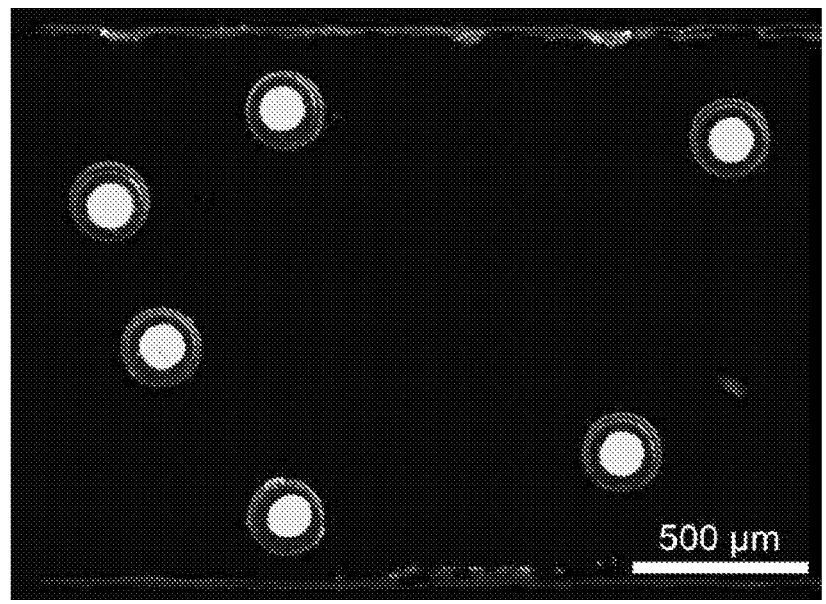
FIG. 8 is an image showing that loaded nanostraw microdevices retain drug after removal from the silicon wafer, according to embodiments of the present disclosure.

FIG. 8. Loaded Nanostraw Microdevices Retain Drug after Removal from the Silicon Wafer.

Nanostraw microdevices were incubated in a PBS solution of 10 mg/mL FITC-insulin overnight, rinsed with and submerged in PBS, and scraped from the wafer with a razor. The PBS-suspended devices were added to a chamber formed by placing an adhesive spacer between a glass slide and a coverslip and incubated at room temperature for 30 min. The devices were then imaged for structure and FITC-insulin localization. FITC-insulin remained within the device reservoirs, indicating that the devices remained sealed following removal from the silicon wafer.

To determine the effect of nanostraws on bioadhesion, microdevices that had undergone RIE to expose nanostraws (FIG. 1H) and microdevices without exposed nanostraws (FIG. 1G) were analyzed with a flow cell adhesion assay. Approximately 400 microdevices were detached from the silicon wafer and incubated in PBS over a monolayer of Caco-2 epithelial cells for 5 min with gentle shaking, facilitating contact between the nanostraw microdevices and the epithelial monolayer. A flow cell was then assembled over the devices, and 20 g/L mucin was passed through the flow cell at increasing rates to achieve stepwise increments of fluid shear stress.

Figure 4:
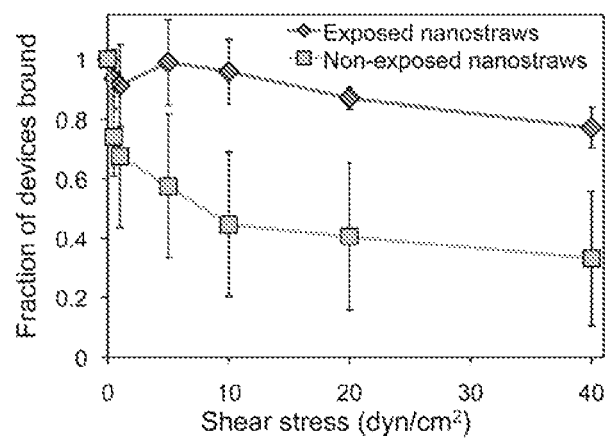
FIG. 4 is a graph showing enhanced bioadhesion of microdevices by nanostraws, according to embodiments of the present disclosure.

The fraction of devices remaining completely adhered to the Caco-2 monolayer following 5 min of flow at each shear stress value was determined. Microdevices with exposed nanostraws demonstrated significantly higher adhesion than control devices (FIG. 4). Following exposure to fluid shear stress values increasing to 40 dyn/cm$^2$, 77±7% of devices with exposed nanostraws and 33±23% of devices without exposed nanostraws remained adhered, demonstrating that nanostraws dramically enhance device bioadhesion. The high fraction of nanostraw microdevices remaining adhered also indicated that bound nanostraw microdevices are likely to remain attached to the intestinal epithelium while under physiological shear stress, which can range from 0.02 to 35 dyn/cm$^2$ during peristalsis.

FIG. 4. Nanostraws Enhance Device Bioadhesion.

Microdevices with nanostraws exposed in the final RIE step or control devices without exposed nanostraws were incubated on a monolayer of epithelial cells and subjected to increasing fluid shear forces within a flow cell. After 5 min at each fluid shear force, fully adhered devices were counted, and the fraction of original devices bound was determined. Microdevices with exposed nanostraws demonstrated significantly higher retention than control devices, indicating that nanostraws enhance device bioadhesion.

Figure 5A:
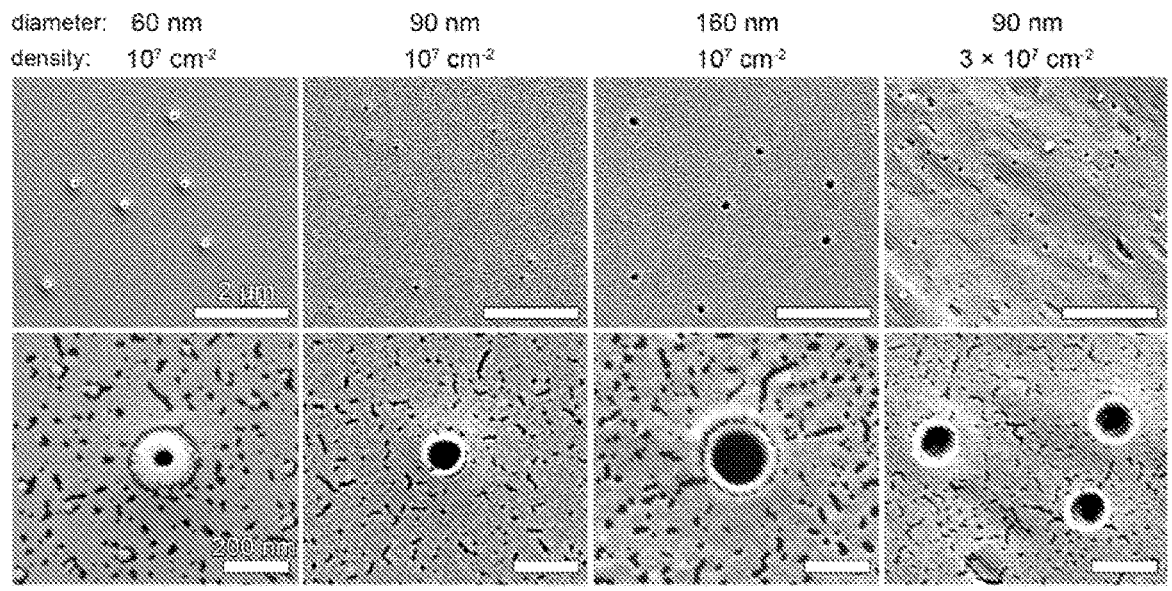
FIGS. 5A-5B are a collection of images and graphs showing tunable release of drug from nanostraw microdevices, according to embodiments of the present disclosure.
Figure 5B:
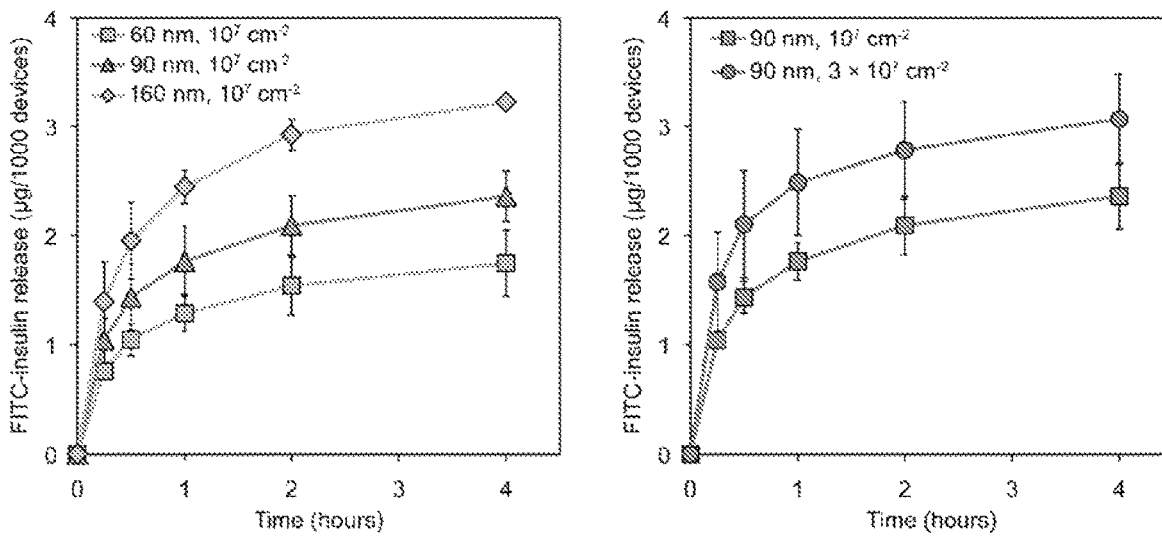

The release rates of FITC-insulin from nanostraw microdevices sealed by nanostraw caps of varying nanostraw inner diameters and densities were monitored (FIG. 5A). For each type of nanostraw membrane, 400-800 devices were incubated in a PBS solution of 10 mg/mL FITC-insulin at 4° C. for 36-48 hours, rinsed in PBS for 1 min, and placed in a PBS solution at 37° C. Drug release was monitored by fluorescence spectroscopy, normalizing to device count (FIGS. 5A-5B). Drug release rates scaled with both nanostraw diameter and density, demonstrating that drug release rates could be tuned by adjusting nanostraw membrane properties.

FIGS. 5A-5B. Drug Release Rates Scale with Nanostraw Diameter and Density, Allowing for Tunable Release.

FIG. 5A. Nanostraw membranes were fabricated with varying nanostraw inner diameters and densities. FIG. 5B. FITC-insulin release rates from microdevices sealed with these membranes scaled with both nanostraw diameter and density, demonstrating tunable drug release.

To test the ability of nanostraw membranes to limit the influx of biomolecules, nanostraw microdevices (inner nanostraw diameter: 60 nm, nanostraw density: $10^7$ cm$^{-2}$) were incubated in 1 mg/mL FITC-dextran (10 kDa) at 37° C. and quantified fluorescence intensity within the device reservoirs over time with confocal fluorescence microscopy (FIG. 6). All fluorescence intensity values were normalized to devices saturated with 1 mg/mL FITC-dextran by incubation at 37° C. for 48 h. 10 kDa FITC-dextran was chosen to model biomolecular diffusion into devices because its hydrodynamic radius (2.3 nm) is similar to digestive enzymes such as trypsin (1.9 nm), chymotrypsin (2.5 nm), and DNase I, (2.5 nm). During incubation in FITC-dextran, the normalized fluorescence intensity in device reservoirs remained below 50% for over 2 hours, suggesting that the nanostraw membrane will reduce the exposure of loaded drug to outside biomolecules relative to a bolus dose, especially within the first few hours of administration.

Figure 6A:
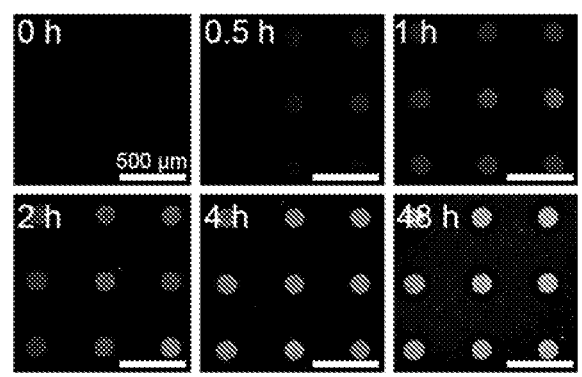
FIGS. 6A-6B are a collection of images and a graph showing that nanostraw membranes limit the influx of outside biomolecules into the device reservoirs, according to embodiments of the present disclosure.
Figure 6B:
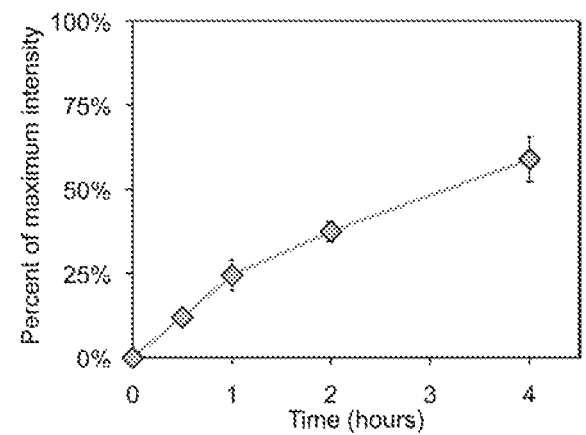

FIGS. 6A-6B. Nanostraw Membranes Limit the Influx of Outside Biomolecules into Device Reservoirs.

Nanostraw microdevices (inner nanostraw diameter: 60 nm, nanostraw density: $10^7$ cm$^{-2}$) were incubated in 1 mg/mL 10 kDa FITC-dextran at 37° C. and imaged with confocal fluorescence microscopy over time to observe FITC-dextran permeation into the device reservoirs (FIG. 6A). This permeation was quantified by integrating fluorescence intensity values in the device reservoirs at each timepoint (FIG. 6B). All values are normalized to devices saturated with 1 mg/mL FITC-dextran.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A microdevice comprising a chamber defining a plurality of sides, wherein the chamber is bound on a first side by a nanoporous membrane comprising:
   a first surface comprising a first region interfacing with the chamber;
   a second surface opposite the first surface; and
   a plurality of hollow nanotubes that extend through the nanoporous membrane from the first surface to a distance above the second surface,
   wherein at least some of the nanotubes extend from within the first region and provide a fluidic conduit between an environment external to the microdevice and the chamber, which is otherwise substantially fluid-tight,
   wherein a layer of a first polymeric material forms one or more second sides bounding the chamber,
   wherein the first polymeric material is selected from poly(methyl methacrylate) (PMMA), polydimethylsiloxane (PDMS), polycarbonate (PC), polyethylene terephthalate (PET), chitosan, poly(lactic-co-glycolic acid) (PLGA), poly-2-hydroxyethyl methacrylate (polyHEMA), polystyrene (PS), polyethylene glycol diacrylate-based hydrogels (PEGDA), co-polymers, mixtures, adducts, or combinations thereof, and
   wherein the nanoporous membrane is bonded to components of the microdevice via one or more second regions of only the first surface.

2. The microdevice of claim 1, wherein the microdevice is a planar device defining a plane, wherein the nanoporous membrane is substantially parallel to the plane.

3. The microdevice of claim 2, wherein the microdevice has a ratio between an average lateral dimension and a thickness of 2:1 or greater.

4. The microdevice of claim 2, wherein the microdevice has a thickness of 1,000 µm or less.

5. The microdevice of claim 2, wherein the microdevice is a substantially circular disc.

6. The microdevice of claim 1, wherein the chamber has a volume in the range of $10^2$ to $10^6$ µm$^3$.

7. The microdevice of claim 1, wherein the nanotubes have an inner diameter in the range of 5 to 1,000 nm.

8. The microdevice of claim 1, wherein the distance above the second surface is in the range of 10 nm to 100 µm.

9. The microdevice of claim 1, wherein the nanoporous membrane comprises the plurality of nanotubes at a density in the range of $10^6$ to $10^9$ cm$^{-2}$.

10. The microdevice of claim 1, wherein the nanoporous membrane is bonded to the first polymeric material of the one or more second sides via a heat-activated, pressure-sensitive adhesive.

11. The microdevice of claim 10, wherein the heat-activated, pressure-sensitive adhesive is selected from polycaprolactone (PCL), poly-L-lactide (PLLA), poly-DL-lactic acid (DL-PLA), polyglycolic acid (PGA), gelatin, agarose, poly(anhydrides), or co-polymers, mixtures, adducts, or combinations thereof.

12. The microdevice of claim 1, wherein the nanoporous membrane comprises a second polymeric material.

13. The microdevice of claim 12, wherein the second polymeric material is selected from polycarbonate (PC), polyethylene terephthalate (PET), polylactic acid (PLA), polyglycolic acid (PGA), PLGA, layer-by-layer polyethylene imine/polyacrylic acid, N-isopropylacrylamide (Ni-PAAM), poly(methyl methacrylate) (PMMA), chitosan, protein hydrogels, or a combination thereof.

14. A kit comprising:
   a microdevice of claim 1; and
   a packaging configured to hold the microdevice.

15. A method of preparing a microdevice, comprising:
   i) fabricating on a substrate a first layer comprising an open chamber comprising a bottom surface and one or more lateral partitions that extend away from the substrate, wherein one or more exposed ends of the one or more lateral partitions distal to the bottom surface define a top surface of the first layer and circumscribe an opening at the top of the chamber;
   ii) bonding a nanoporous membrane to the top surface, thereby forming a fluid-tight seal between the top surface and the nanoporous membrane, wherein the bonding comprises:
   depositing a second layer of a heat-activated, pressure-sensitive adhesive on the top surface; and
   heat bonding the nanoporous membrane to the top surface, wherein the nanoporous membrane comprises:
   a first surface comprising a first region interfacing with the chamber; and
   a second surface opposite the first surface; and
   a plurality of hollow nanotubes that extend through the nanoporous membrane from the first surface to the second surface;
   iii) patterning the first layer and the nanoporous membrane bonded to the top surface; and
   iv) removing a sublayer of the patterned nanoporous membrane, thereby forming a third surface of the nanoporous membrane opposite the first surface, wherein the nanotubes extend through the nanoporous membrane from the first surface to a distance above the third surface,
   wherein at least some of the nanotubes extend from within the first region and provide a fluidic conduit between an environment external to the microdevice and the chamber, which is otherwise substantially fluid-tight.

16. The method of claim 15, wherein the heat-activated, pressure-sensitive adhesive is polycaprolactone (PCL), poly-L-lactide (PLLA), poly-DL-lactic acid (DL-PLA), polyglycolic acid (PGA), gelatin, agarose, poly(anhydrides), or co-polymers, mixtures, adducts, or combinations thereof.

* * * * *